United States Patent [19]

Grammont et al.

[11] Patent Number: 5,074,882
[45] Date of Patent: Dec. 24, 1991

[54] PROGRESSIVE ELONGATION CENTRO-MEDULLAR NAIL

[75] Inventors: Paul Grammont, Dijon; Jean M. Guichet, Dijon Cedex, both of France

[73] Assignee: Medinov SARL, France

[21] Appl. No.: 340,466

[22] Filed: Apr. 19, 1989

[30] Foreign Application Priority Data

Jun. 9, 1988 [FR] France .................. 88 08099

[51] Int. Cl.$^5$ ........................ A61F 2/34; A61F 5/04
[52] U.S. Cl. ........................... 623/23; 606/63
[58] Field of Search ................ 623/16, 18, 19, 20, 623/22, 23; 606/63, 64, 57

[56] References Cited

U.S. PATENT DOCUMENTS

| | | | |
|---|---|---|---|
| 3,680,553 | 8/1972 | Seppo | 606/64 |
| 4,157,715 | 6/1979 | Westerhoff | 606/63 |
| 4,262,665 | 4/1981 | Roalstad et al. | 606/63 |
| 4,384,373 | 5/1983 | Sivash | 623/18 |
| 4,453,539 | 6/1984 | Raftopoulos et al. | 606/63 |
| 4,502,160 | 3/1985 | Moore et al. | 623/18 |
| 4,892,546 | 1/1990 | Kotz et al. | 623/18 |

OTHER PUBLICATIONS

F. Baumann et al, "Der Verlangerungsnagel," *Archiv fur orthopadische and Unfall-Chirurgie*, vol. 90, pp. 139–146 (1977).
J. Gotz et al, "Kontinuierliche Verlangerung des Femur bei intramedullarer Stabilisierung," *Arch. orthop. Unfall-Chir.*, vol. 82, pp. 305–310 (1975).
A. N. Witt et al., "Tierexperimentelle Ergebnisse mit einem voll implantierbaren Distraktionsgerat zur operativen Beinverlangerung," *Archiv fur orthopadische und Unfall-Chirurgie*, vol. 88, pp. 273–279 (1977).
G. J. Verkerke et al., "A Lengthening Element for a Modular Femur Dndoprosthetic System," 35th Annual Meeting, Orthopaedic Research Society, Feb. 6–9, 1989, Las Vegas, NV, p. 494.
A. I. Bliskunov, "Prodlouzeni Stehenni Kosti Implantovatelnymi Aparaty," *Acta Chir. orthop., Traum. cech.*, vol. 51, No. 6, pp. 451–466 (1984).
A. I. Bliskunov, "Implantable devices for Thigh Lengthening Without External drives," *Priorov Central Scientific-Research Institution for Traumatology and Orthopedics*, pp. 44–49 (1982).
A. I. Bliskunov, "Elongation of the Femur by Means of Controlled [Manipulated], Implanted Structures," (Experimental-Clinical Research), Dissertation for Completion of Doctorate in Medical Sciences.

*Primary Examiner*—David J. Isabella
*Attorney, Agent, or Firm*—Mason, Fenwick & Lawrence

[57] ABSTRACT

A device including a nail for gradually lengthening long bones including outer and inner sliding tubes connected by a double ratchet mechanism, the nail being fixed by its two extremities in the bone, and the device being entirely included in the concerned bone, being lengthened post-operatively by maneuvers applied on the limb. Rotation of a distal part of the limb with respect to proximal part of the limb allows rotation of the ratchet mechanism with lengthening of the device in one direction, and keeping of the gained length in the other direction while returning to the neutral axis of the rotation of the device, thereby featuring a dynamization system, and a system, to limit the range of rotation of the device.

20 Claims, 3 Drawing Sheets

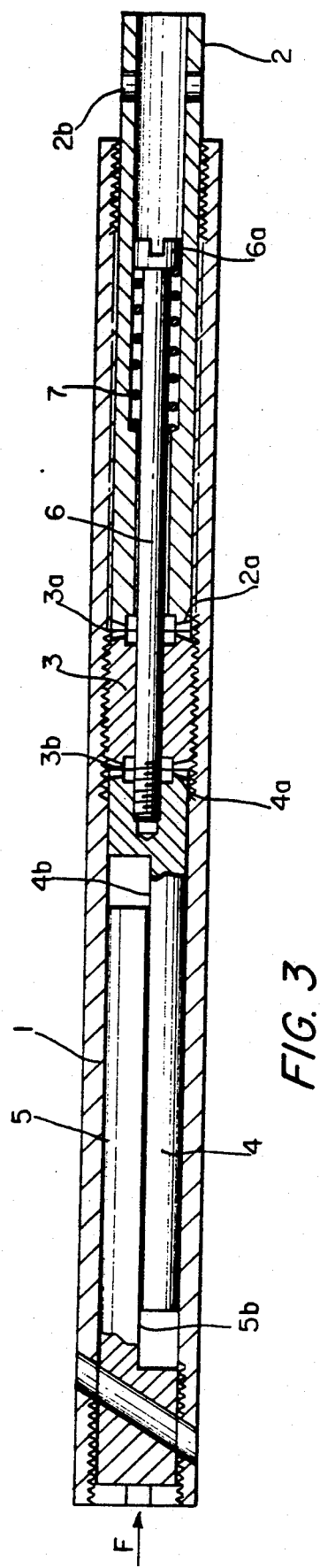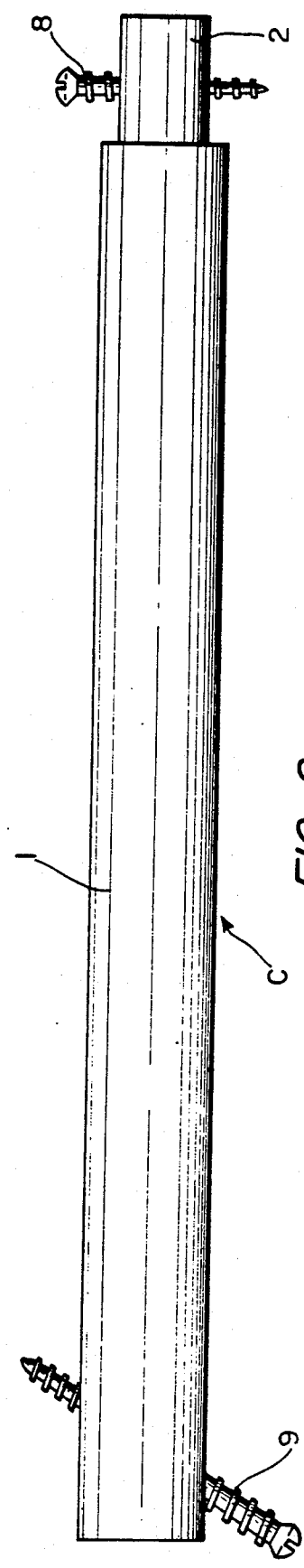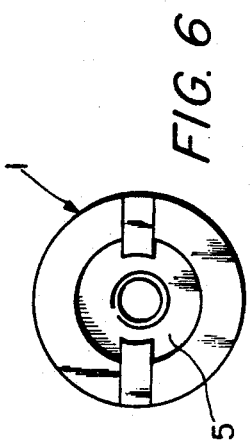

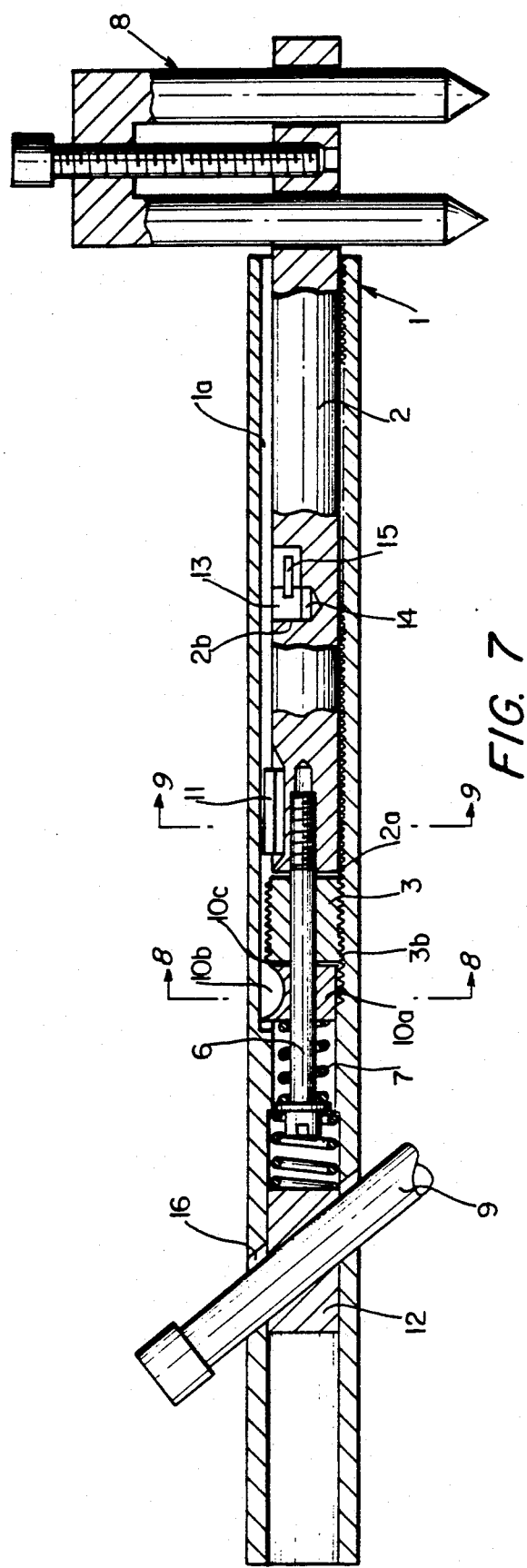
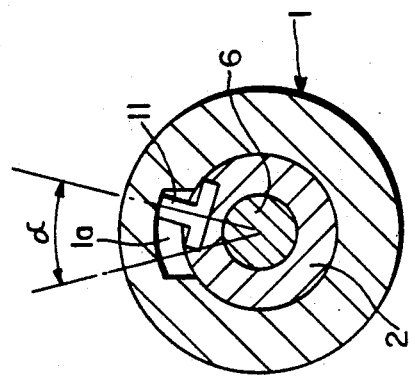

PROGRESSIVE ELONGATION CENTRO-MEDULLAR NAIL

FIELD OF THE INVENTION

The invention relates to the medical techniques for prothesis used in orthopedic surgury, and more particularly to surgical implants for lengthening of limbs or of the extremities.

More particularly, the invention relates to an expandable intramedullary nail disposed inside a patient and configured for insertion into a medullary cavity of the patient's limb containing a bone and constructed so as to be fixed with a view to making it integral which at least two distal parts of the bone, the nail consisting of a system or sub-system (1, 2, 3, 4 and 5) including a fixing mechanism, that progressively elongates, wherein the system, except the fixing machanism, is fully disposed within the medullary cavity.

BACKGROUND OF THE INVENTION

It is known that after congenital malformations or anomalies, or even after fractures, losses of osseous or other substances, certain bones such as the humerus, femur, tibia, atc., are too short, thus creating asymmetry or hypometry. In the case of lower limbs with slight asymmetry, less than 3 centimeters, orthopedic treatment is called for by adding, for example, a shoe or other orthopedic apparatus to the limb which is short. With asymmetry or hypometry which is more significant, in order to elongate the shorter limb, surgical solutions currently using two types of means exist:

External fixtures—an operation is made using external apparatus on certain parts of which, for example, metal pins, etc., go through the soft tissues to reach the bone of which they are an integral part. The apparatus can be seen from outside the limb. The advantage of such apparatus which is therefore accessible fron outside of the limb, is to be able to act on the apparatus at determined periods of time in order to consequently provoke a certain degree of elongation of the bone in a progressive manner generally at the diaphysis of the bone after cutting the latter. However, problems regarding attractiveness are encountered as the user has difficulties in putting up with such apparatus and risks of infection are not negligible; and Internal fixtures: the second solution consists of taking action from the inside, i.e., no element can be seen from outside the limb. For this purpose, centro-medullar nails or intramedullary nails are generally used or osteosynthesis plates which are suitably fixed to the bone.

The advantage of this solution with respect to the previous one, lies in the fact that no element can be seen from outside the limb. On the other hand, the bone cannot be progressively elongated. However, a quite significant elongation can be carried out thanks to repeated surgical interventions which are consistent each time in obtaining a fixed but limited elongation due to elastic and plastic limits of the soft tissues on stretching. In the case of non-progressive significant elongation, the compensation of the dimensional deviation is risky and requires adjuvants to the osteosynthesis, e.g. grafts, etc., which reduce the mechanical and physiological properties of the elongated bone.

No strictly internal fixing system, fully imbedded into the patient, currently exists which enables a limb to be elongated progressively with a mechanism incorporated into the fixing system, either automatically moved or moved by external action on the limb.

DESCRIPTION OF THE PRIOR ART

Various prior art of gradual intramedullary nails, and the like, as well as apparatus and method of their construction in general, are found to be known, and exemplary of the U.S. prior art are the following:

| Seppo | 3,680,553 |
|---|---|
| Westerhoff | 4,157,715 |
| Roalstad | 4,262,665 |
| Sivash | 4,384,373 |
| Raftopoulos | 4,453,539 |
| Moore | 4,502,160 |
| Kotz | 4,892,546 |
| Keller | EP 0212 192 |
| Scales | GB 2 13 137 884 A |
| Bauman | DE 027 05 154 A1 |

The device of Seppo is a fixing apparatus for osteosynthesis of fractures, and includes a complex mechanism that does not feature a lengthening function. Westerhoff can be considered as a lengthening device effected solely by means of a small pump which is set out of the cylindrical device. Roalstad does not feature a lengthening function, but is an intermedullary compression device set during the surgical procedure and not capable of being modified thereafter. Raftopoulos discloses an expandable intramedullary device having an expandable part acting as a locker in the bone, and has no lengthening function.

These patents or known prior uses teach and disclose various types of devices of sorts for intramedullary devices and lengthening prosthetic joint implants and of various manufactures and the like as well as methods of their construction, but none of them whether taken singly or in combination disclose the specific details of the combination of the invention in such a way as to bear upon the claims of the present invention.

SUMMARY OF THE INVENTION

The object of the invention is to create this new system of elongation which combines the advantages of progressive elongation of the external fixtures which are adjusted at will with the advantages of internal fixtures without the disadvantages of these two fixing systems.

Another advantage of the invention is to provide a method and apparatus according to which means is used to enable the bone to be treated to be elongated, is firstly, internally fixed internally without there being any part seen from outside the limb, and secondly, constructed so as to progressively and modulably act on the degree of elongation. In order to overcome this problem, a centro-medullar nail or intramedullary nail is constructed and developed so as to be fixed with a view to being integral to at least two parts of the same long bone, cut into parts, the nail being constructed of several components for it to provide progressive elongation of the nail after partial rotation applied by external action on the limb concerned and/or automatically obtained during the physiological movement, such as walking, etc., of the limb and the holding in this position of elongation after each rotation applied to the limb and return to a neutral position of the osseous parts of the segments of the limb concerned.

Another object of the invention is to provide a barrel with a tube mounted inside capable of moving in translation, the tube being fitted with means to relatively move the tube and barrel under an effect of rotational movements applied to the limb in one direction in order to correspond with the elongation and in the other rotational direction to lock the tube and barrel in translation.

Another object of the invention is to provide the tube coupled to a threaded bush threaded into the bore of the barrel which is tapped for this purpose, either totally or partially, the bush being constructed firstly in combination with one part of the tube, and secondly, with locking means to allow, in combination and one direction, the threaded bush to be rotated in order to concomitantly move by rotation and translation the tube and barrel and in the other direction the locking of the bush in order to prevent the tube moving in translation in the barrel.

A further object of the invention is to provide fittings on the threaded seating made up of ratchet systems which are positioned at each end of the seating, each ratchet system being reversed.

A further object of the invention is to provide locking means which is not capable of rotating but moving in translation with respect to the barrel and which cooperates with the bush, made up of two complementary cylindrical rods each with a seating with a flat and the seatings being interlaced. The interlacing seatings have a round section, and one of the rods locks the locking means in rotation with respect to the barrel, and the other rod is fitted in combination with the threaded bush.

A further object of the invention is to provide a system in which the threaded bush, the sliding tube and the locking means are held under pressure by a screw, rivet, or other means to fulfil a compression function.

A further object of the invention is to provide a system in which a screw or compression means inserted inside the sliding tube and the bush in order to be threaded or fixed into one of the cylindrical rods, or other means to fulfil the locking function, the head of the screw or a shoulder of the compression means cooperating with an elastic means applied against a shoulder of the bore of the tube. Different mechanical constructions of the compression means and the elastic means can be anticipated, however, they must comply with the operating principle of the components of the nail of the invention, i.e., fulfil the same function of compressing the tube, bush and locking means.

A further object of the invention is to provide another embodiment in which the locking means which cooperates with the bush are made up of a key system cooperating with a groove system formed in the bore of the barrel.

A further object of the invention is to provide in an advantageous manner the key locking system which comprises a cylindrical body supporting at least one key inserted into the grooves, the body cooperating with the bush whilst being held by compression by the component in the form of an axial compression system of the screw, rivet or other type freely inserted into the thickness of the body and the bush being fixed into one part of the tube, and the system cooperating with an elastic means.

According to another feature of the invention, the tube and the barrel have combined complementary fittings to limit the relative angular movement of the tube and the barrel. On the one hand, the sliding tube and one of the ends of the barrel, along with the end of the cylindrical rod opposite the bush on the other hand, have fittings for fixing the nail into the bone.

In order to overcome the problem of slightly stressing the osseous callus by compression which turns out to be very advantageous in order to accelerate the density of the bone at the end of the elongation without disturbing the elongation phase as such, one of the fixing components is angularly engaged into the thickness of the barrel in a slot through a bush mounted so as to freely slide into the barrel in order, in combination with elastic means and to provide limited linear movement in translation of the barrel with respect to the fixing component.

In order to solve another problem prohibiting any relative elongation movement of the nail at the end of the treatment, the barrel and the tube have, in combination, means constructed so as to be controlled from outside the limb, or automatically controlled for the desired elongation, obtained with incorporated control of the nail, or simple locking, positioned so as to stop the tube from sliding in the barrel once the elongation has been obtained, the means being to angularly and longitudinally lock the sliding tube and barrel.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWINGS

FIG. 1 is a perspective and exploded view showing the different components of the nail according to a preferred embodiment of the present invention.

FIG. 2 is a front view of the nail.

FIG. 3 is a longitudinal sectional view of the nail.

FIG. 6 is an end view according to arrow F according to FIG. 3.

FIG. 7 is a longitudinal sectional view of the nail according to another embodiment of the invention.

FIG. 8 is a sectional view taken along the lines 8—8 of FIG. 7.

FIG. 9 is a sectional view taken along the lines 9—9 of FIG. 7.

DETAILED DESCRIPTION OF THE PREFERRED EMBODIMENTS

Figure 4:
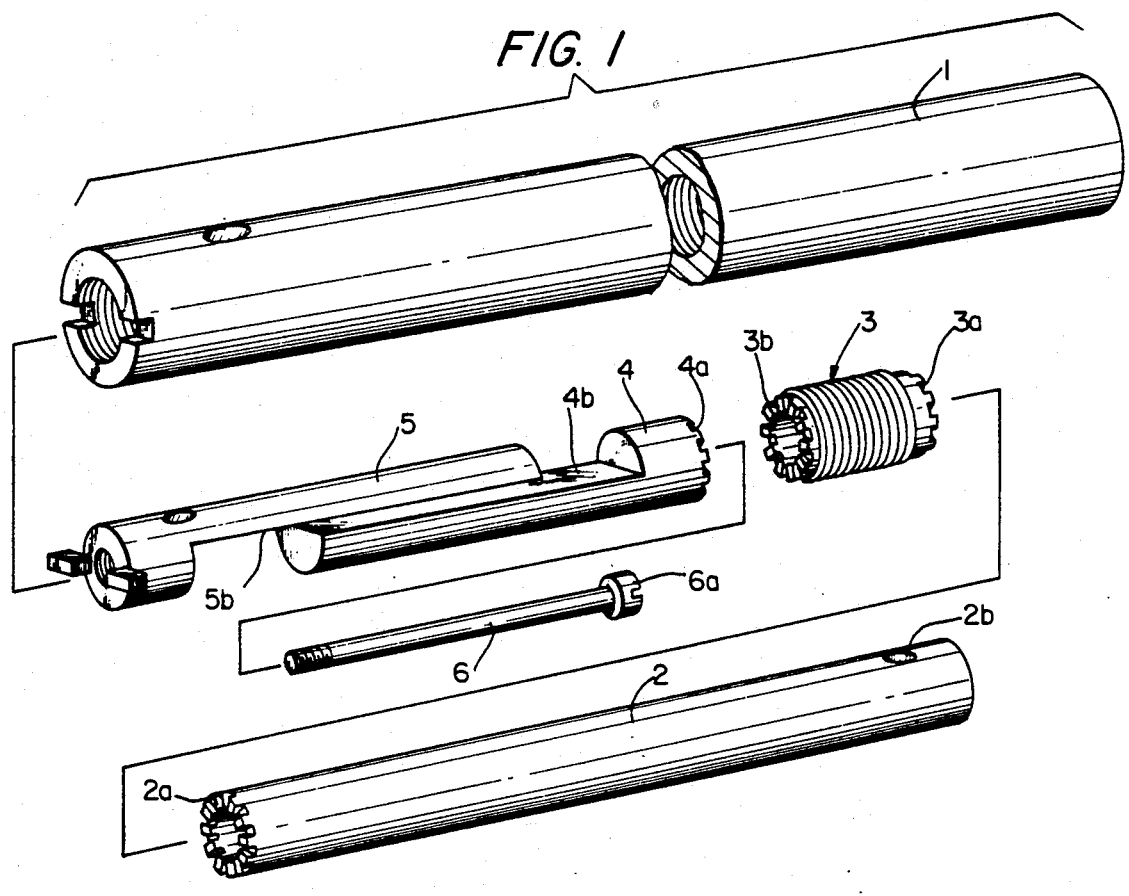
FIG. 4 and 5 are schematic views showing the fixing and the operation principle of the nail of the invention.

Referring now to the drawings is a nail C (in FIG. 2) to be positioned inside the medullar canal of a bone with a view to provoking its elongation and thus creating a dimensional deviation between the osseous fragments in order to suppress the shortening due, for example, to a congenital problem, a fracture, or loss of an osseous substance. The nail C is generally fixed to the level of the diaphysis, either side of the cut fragment of bone and comprises a tubular barrel 1 inside of which is mounted with the capacity of movement in translation, a tube 2. According to the invention, the barrel 1 and the tube 2 are fixed with elements or means, such as bush 3, rods 4, and rods 5 to provoke under the rotational effect of an external action of the distal part of the cut fragment, in one direction, the relative movement in translation of the barrel and tube corresponding to an elongation and, in the other direction, the locking of the tube 2 and barrel 1 in to a priorly mentioned positioned. In one form of the embodiment of the invention illustrated, the tube 2 is servocontrolled by a threaded bush 3 threaded into the bore of the barrel 1 which is tapped as a consequence either totally or partially. With the aim sought-after in mind, this bush 3 is fitted in combination firstly, with the sliding tube 2 and secondly, the locking means 4–5 so as to be turned in a certain rotational direction applied to the limb which corresponds to a movement of the tube 2 and locked in rotation in the opposite direction so as to move in translation. Each of the ends of the threaded bush 3 have frontal ratchet systems 3a and 3b and each of the ratchet systems 3a and 3b have inverted teeth in order to create the below-mentioned opposite effects. One of the ratchet systems 3a of the bush 3 cooperates with complementary teeth 2a frontally formed on one end of the tube 2. The other ratchet system 3b cooperates with complementary teeth 4a frontally formed at the end of an assembly comprised of two complementary cylindrical rods 4 and 5 making up the locking means. With this objective each of the rods 4 and 5 have a semi-circular seating 4b and 5b being interlaced in order to consequently enable the relative sliding of the rods and their angular locking in rotation.

The assembly of component elements of the tube 2, bush 3 and rod 4 are compressed with respect to one another by means of a screw 6. This screw 6 is freely engaged inside the tube and the bush 3 so as to be threaded into the cylindrical tube 4. The head 6a of the screw 6 is applied against a compression spring 7 mounted in the bore of the tube 2 applied against a shoulder 2a. An end projecting from the tube 2 opposite the bush 3 has, transversely, a breaking-through hole 2b or other fitting, for the passage of a fixing component of the screw type 8. In the same way, the end opposite the barrel 1 and the rod 5 are transversely pierced through for the passage of a fixing component of the screw type 9.

In another embodiment as shown in FIGS. 7, 8, and 9, the device for locking in rotation comprised of the rods 4 and 5 is replaced by a key system 10 cooperating with a groove system 1a formed in the bore of the barrel 1 to provide the guiding in translation whilst locking the rotation. As FIGS. 7 and 8 show, the key locking system 10 comprises a cylindrical body 10a supporting the key 10b engaged into the groove system 1a, the body cooperating, through one of its faces 10c with the teeth of one of the ratchet systems 3b of the bush 3. As previously, the other ratchet system 3a of the bush 3 cooperates with the complementary teeth 2a of the tube 2. Similarly, all components 10, 2 and 3 are compressed by the screw 6 fixed to the compression spring 7. The screw 6 is freely engaged into the thickness of the body 10a and the bush 3 whilst being threaded into part of the tube 2.

In an advantageous manner, the groove system 1a can be used in order to limit the rotation of the tube 2 with respect to the barrel or vice versa. For this purpose, the tube 2 has a key 11 or such like component, to cooperate with the groove system 1a with the capacity of limited angular movement a under the driving effect of the tube. This angular movement a is determined in order to correspond with the value of a tooth of the ratchet system of the bush 3 (see FIG. 9).

In the embodiment illustrated in FIG. 7, the fixing component 9 is angularly engaged into the thickness of the barrel 1 in a slot 1b and through a bush 12 mounted so as to freely slide inside the barrel. The bush 12 is fixed to a spring 16. Therefore it appears that the barrel 1 is likely to be moved linearly in translation with respect to the fixing component 9 of a limited value. Given these conditions, at every step, the osseous callus is slightly stressed by compression, which turns out to be very advantageous in order to accelerate the densification of the bone at the end of the elongation process without disturbing the elongation phase as such.

Figure 5:
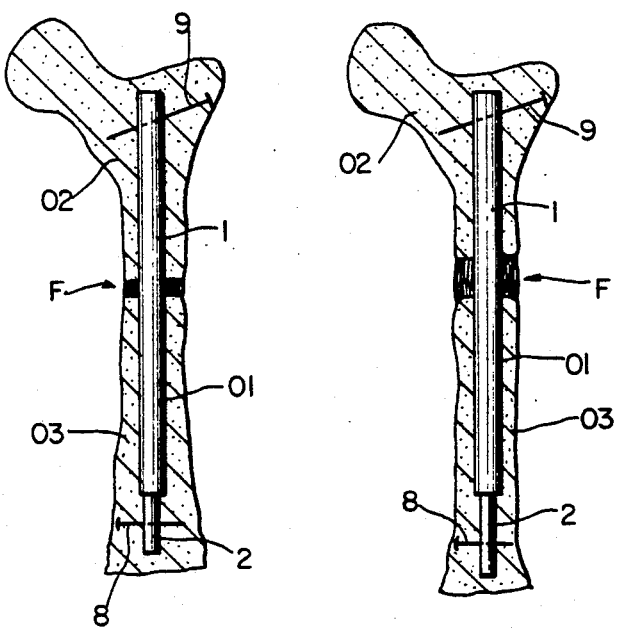

Considering this and the various fittings of the centro-medullar nail, the following operation results:

The nail C is introduced in a known manner inside the medullar canal 01 in FIGS. 4 and 5 of the bone to be treated which was cut at the osteotomy focus F. The two parts of bone situated either side of the osteotomy focus are identified as 02 and 03.

Given these conditions, the nail is fixed either side of the osteotomy focus by means of screws 8 and 9 respectively engaged into parts of bone 02 and 03, cooperating firstly, with the end projecting from the tube 2 and secondly, the barrel 1, FIG. 4. Therefore, it appears that under the effect of rotation, by external action of the distal part of the cut fragment, parts 02 and 03 would be subjected to a rotational torque. The barrel 1, for example, remaining fixed in rotation, under the effect of the torque, the tube 2 and concomitantly the threaded bush 3 would be rotated which would provoke the movement in translation of the tube 2 corresponding to an elongation of the length of the nail in function of the pitch of the thread of the bush. The concomitant rotation of the tube 2 and the bush in a certain direction of the rotation applied, results from the ratcheting system 2a–3a which is in a coupling position by its profile of teeth, whereas the other ratcheting system 3b–4a is in a free non-driving position.

Inversely, in the other direction of the rotation torque, the ratcheting system 2a–3a is in a free position so that the rotation of the tube 2 is carried out without effecting the bush 3 which, furthermore, is locked in rotation by the system of rods 4–5 or the key 10 and groove system 1a, consequently prohibiting the reverse movement in translation of the movement of translation of the tube 2. Therefore it can be seen that on each effect of rotational movement applied to the limb, there will be relative movement in translation of the tube 2 and barrel 1, corresponding to an elongation of the nail and consequently the bone (see FIG. 5).

An aim sought-after is therefore, attained considering that the elongation is carried out in a progressive and willing manner whilst respecting the problem initially brought up, i.e., having no external element.

It is to be noted that at the end of the treatment, when the desired length of the bone has been reached, the elongation function of the nail such as defined, is prohibited so that it remains in a position which is locked in translation. For example, the minimum surgical intervention can be envisaged in order to simplify fit of the pin or other means likely to lock the tube 2 in rotation with respect to the barrel 1. For example, a finger 13 fixed to a spring 14 is mounted in the housing 2b of the tube whilst being likely to cooperate with the groove system 1a. This finger is locked in the retracted position, i.e., in the disengagement position of the groove system 1a by a retractable pin 15 actuated by a magnet or other means from outside the limb. When the pin is disengaged, under the slackening effect of the spring 14, the finger 13 is engaged into the groove system 1a thus provoking the angular locking of the tube 2 with respect to the barrel 1 so as to consequently prevent any elongation movement.

Obviously other systems likely to fulfil the same or like functions may be envisaged; for example, the finger 5 may be actuated by a mechanism incorporated into the nail and automatically triggered without excluding any system only locking the relative movements of the sliding tube in the barrel when the desired elongation is obtained.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

We claim:

1. An intramedullary nail for use in a medullary cavity of a patient's bone, said nail comprising:
   an elongated hollow barrel;
   an elongated tube movably mounted within said barrel, one end of said tube being disposed within a hollow portion of said barrel and an other end of said tube being outside of said barrel;
   locking means positioned within the hollow portion of said barrel, said locking means having first and second opposed ends;
   means for securing said first end of said locking means against rotation within said barrel; and
   position-controlling means positioned within said barrel, said position-controlling means cooperating with the hollow portion of said barrel, said one end of said tube and said second end of said locking means, wherein rotation of said tube relative to said barrel in a first direction causes said position-controlling means to operate in a first manner to move said tube out of said barrel a predetermined amount, while said locking means prevents operation of said position-controlling means to maintain the relative longitudinal positions of said barrel and said tube when said tube rotates in a direction opposite to said first direction.

2. The intramedullary nail of claim 1, wherein said locking means comprises:
   a first cylindrically-shaped rod having a first transverse surface at one end of said first rod, the other end of said first rod forming said first end;
   a second cylindrically-shaped rod having a second transverse surface at one end of said second rod, the other end of said second rod forming said second end, said first and second surfaces complementing each other so that said first and second rods overlap and translate relative to each other within said hollow barrel; and
   said securing means secures said first rod against rotation within said barrel and limits the movement of said second rod along the longitudinal axis of and within said hollow barrel.

3. The intramedullary nail of claim 2, wherein said first and second transverse surfaces are each planar.

4. The intramedullary nail of claim 1, wherein said position-controlling means comprises:
   an interior threaded portion defined within the hollow portion of said barrel;
   a bush threadly engaged with said interior threaded portion, said bush terminating in first and second ends;
   a first ratchet means defined by said first end of said bush and said one end of said tube; and
   a second ratchet means defined by said second end of said bush and said second end of said locking means, wherein rotation of said tube relative to said barrel in a first direction causes said first ratchet means to rotate said bush in a first direction to move said tube out of said barrel by a predetermined amount, while said locking means prevents rotation of said bush back into said barrel when said tube rotates in a direction opposite to said first direction.

5. The intramedullary nail of claim 4, wherein said locking means comprises:
   a first cylindrically-shaped rod having a first transverse surface at one end of said first rod, the other end of said first rod forming said first end;
   a second cylindrically-shaped rod having a second transverse surface at one end of said second rod, the other end of said second rod forming said second end, said first and second surfaces complementing each other so that said first and second rods overlap and translate relative to each other within said hollow barrel; and
   second securing means secures said first rod against rotation within said barrel and limits the movement of said second rod along the longitudinal axis of and within said hollow barrel.

6. The intramedullary nail of claim 5, further comprising means for urging said tube in the direction of said bush to facilitate the operation of said first ratchet means.

7. The intramedullary nail of claim 6, wherein said means for urging is a compression spring.

8. The intramedullary nail of claim 5, further comprising means for urging said second end of said locking means in the direction of said bush to facilitate the operation of said second ratchet means.

9. The intramedullary nail of claim 1, wherein said hollow barrel has longitudinally-extending bore, and wherein said position-controlling means comprises:
   a bush terminating in first and second ends;
   first and second translation means cooperating to limit the rotation of said tube within said bore, said first translation means defined on said barrel within said bore and said second translation means defined on said tube;
   a first moving means defined on said first end of said bush and said one end of said tube;
   means for securing said first end of said locking means to said barrel; and
   a second moving means defined on said second end of said bush and said second end of said movement limiting means, wherein rotation of said tube relative to said barrel in a first direction causes said first moving means to rotate said bush in a first direction to move said tube out of said barrel by a predetermined amount, while said locking means prevents rotation of said bush back into said barrel when said tube rotates in a direction opposite to said first direction.

10. The intramedullary nail of claim 1, further comprising:
    first securing means defined on the end of said barrel remote from where said tube emerges from said barrel for securing said nail to one end of the patient's bone; and second securing means defined on the other end of said tube for securing said nail to another end of the patient's bone.

11. The intramedullary nail of claim 1, wherein said locking means comprises:
   a longitudinally-extending groove defined within said longitudinally-extending bore;
   a cylindrical member movably mounted within said bore; and
   a longitudinally-extending key member mounted on the outer surface of said cylindrical member and positioned within said groove to limit rotational movement of said cylindrical member within said bore.

12. The intramedullary nail of claim 11, wherein said key member positioned within said groove confines movement of said cylindrical member along the longitudinal axis of said barrel.

13. The intramedullary nail of claim 11, wherein said cylindrical member includes a mounting groove for supporting the engagement of said key within said groove defined in said bore.

14. The intramedullary nail of claim 9, further comprising means affixed to the exterior surface of said tube and cooperating with said groove defined in the bore of said barrel for limiting the relative angular movement of said tube within said barrel.

15. The intramedullary nail of claim 1, further comprising means for fixing the position of said tube relative to said barrel.

16. The intramedullary nail of claim 15, wherein said fixing means comprises:
   a hollow volume defined within said tube;
   a finger movably mounted within said hollow volume;
   means for fixing said finger in a retracted position within said hollow volume; and
   disengaging means for moving said finger into engagement with said groove in said bore of said barrel.

17. The intramedullary nail of claim 16, wherein said disengaging means is magnetically actuated.

18. The intramedullary nail of claim 9, further comprising means for urging said tube in the direction of said bush to facilitate the operation of said first ratchet means.

19. The intramedullary nail of claim 18, wherein said means for urging is a compression spring.

20. The intramedullary nail of claim 9, further comprising means for urging said second end of said locking means in the direction of said bush to facilitate the operation of said second ratchet means.

* * * * *